United States Patent [19]
Butler et al.

[11] Patent Number: 5,902,745
[45] Date of Patent: May 11, 1999

[54] CELL ENCAPSULATION DEVICE

[75] Inventors: Mark D. Butler; Paul D. Drumheller; Stanley L. Mish, all of Flagstaff, Ariz.

[73] Assignee: Gore Hybrid Technologies, Inc., Flagstaff, Ariz.

[21] Appl. No.: 08/859,946

[22] Filed: May 21, 1997

Related U.S. Application Data

[63] Continuation of application No. 08/532,925, Sep. 22, 1995, abandoned.

[51] Int. Cl.$^6$ .................................................. C12M 3/06
[52] U.S. Cl. ........................... 435/297.2; 435/297.1; 435/182; 435/382; 424/424; 424/93.7
[58] Field of Search ........................... 435/174, 182, 435/180, 382, 400, 401, 297.1, 297.2, 307.1, 309.1, 308.1, 309.2; 604/890.1, 891.1, 892.1; 424/424, 93.7

[56] References Cited

U.S. PATENT DOCUMENTS

| | | |
|---|---|---|
| 3,993,072 | 11/1976 | Zaffaroni . |
| 4,113,912 | 9/1978 | Okita . |
| 4,193,138 | 3/1980 | Okita . |
| 4,298,002 | 11/1981 | Ronel et al. . |
| 4,353,457 | 10/1982 | Sun et al. . |
| 4,353,888 | 10/1982 | Sefton . |
| 4,378,016 | 3/1983 | Loeb . |
| 4,391,909 | 7/1983 | Lim . |
| 4,409,331 | 10/1983 | Lim . |
| 4,420,589 | 12/1983 | Stoy . |

(List continued on next page.)

FOREIGN PATENT DOCUMENTS

| | | |
|---|---|---|
| 0 213 908 | 3/1987 | European Pat. Off. . |
| 0 290 166 | 11/1988 | European Pat. Off. . |
| 0 331 521 | 9/1989 | European Pat. Off. . |
| 0 359 575 | 3/1990 | European Pat. Off. . |
| 0 457 430 | 11/1991 | European Pat. Off. . |
| 0 504 781 | 9/1992 | European Pat. Off. . |
| 0 147 939 | 7/1995 | European Pat. Off. . |
| WO 84/01287 | 4/1984 | WIPO . |
| WO 90/01498 | 2/1990 | WIPO . |
| 90/02170 | 3/1990 | WIPO ..................... 435/297.2 |
| WO 90/12604 | 11/1990 | WIPO . |
| WO 90/15637 | 12/1990 | WIPO . |
| WO 91/00119 | 1/1991 | WIPO . |
| WO 91/10425 | 7/1991 | WIPO . |
| WO 91/10470 | 7/1991 | WIPO . |
| WO 92/07525 | 5/1992 | WIPO . |
| WO 92/19195 | 11/1992 | WIPO . |
| WO 93/08850 | 5/1993 | WIPO . |
| WO 93/19701 | 10/1993 | WIPO . |
| WO 93/21902 | 11/1993 | WIPO . |
| WO 93/22427 | 11/1993 | WIPO . |
| WO 94/07999 | 4/1994 | WIPO . |
| WO 95/01203 | 6/1994 | WIPO . |
| WO 95/04521 | 6/1994 | WIPO . |
| WO 95/18583 | 7/1995 | WIPO . |

OTHER PUBLICATIONS

Altman et al., "Long–Term Plasma Glucose Normalization in Experimental Diabetic Rats With Macroencapsulated Implants of Benign Human Insulinomas," *Diabetes*, 35:625–633 (1986).

(List continued on next page.)

*Primary Examiner*—William H. Beisner
*Attorney, Agent, or Firm*—Eric J Sheets

[57] ABSTRACT

The present invention is directed to a cell encapsulation device that permits rapid and straightforward cell transfer into the device. The preferred device includes components that allow a user to quickly transfer cells into the device with minimal risk to the cells. Among the most important improvements of the present invention are: automatic filtration of excess solution during cell transfer; an instantly wettable cover, allowing ready view into the cell chamber; and a swellable core, allowing cells to be transferred with minimal shear force while assuring optimal cell placement in the device during use. The device of the present invention may be used either in vivo, such as to deliver therapeutic substances, or in vitro, such as to serve as a bioreactor.

10 Claims, 4 Drawing Sheets

U.S. PATENT DOCUMENTS

| | | |
|---|---|---|
| 4,487,758 | 12/1984 | Goosen et al. |
| 4,495,288 | 1/1985 | Jarvis, Jr. et al. |
| 4,505,266 | 3/1985 | Yannas et al. |
| 4,631,188 | 12/1986 | Stoy et al. |
| 4,663,286 | 5/1987 | Tsang et al. |
| 4,673,566 | 6/1987 | Goosen et al. |
| 4,686,098 | 8/1987 | Ko pchick et al. |
| 4,722,898 | 2/1988 | Errede et al. |
| 4,743,545 | 5/1988 | Torobin |
| 4,789,550 | 12/1988 | Hommel et al. |
| 4,803,168 | 2/1989 | Jarvis, Jr. |
| 4,806,355 | 2/1989 | Goosen et al. |
| 4,892,538 | 1/1990 | Aebischer et al. |
| 4,902,295 | 2/1990 | Walthall et al. |
| 4,911,717 | 3/1990 | Gaskill, III. |
| 4,941,812 | 7/1990 | Samelson |
| 4,942,129 | 7/1990 | Goosen et al. |
| 4,969,705 | 11/1990 | Stoy et al. |
| 4,997,443 | 3/1991 | Walthall et al. |
| 5,002,661 | 3/1991 | Chick et al. |
| 5,011,486 | 4/1991 | Aebischer et al. |
| 5,017,490 | 5/1991 | Taiariol et al. |
| 5,030,255 | 7/1991 | Aebischer et al. |
| 5,068,195 | 11/1991 | Howell et al. ........................ 435/297.2 |
| 5,081,035 | 1/1992 | Halberstadt et al. |
| 5,084,350 | 1/1992 | Chang et al. |
| 5,100,392 | 3/1992 | Orth et al. |
| 5,106,627 | 4/1992 | Aebischer et al. |
| 5,109,866 | 5/1992 | Guegan et al. |
| 5,116,493 | 5/1992 | Chick et al. |
| 5,116,494 | 5/1992 | Chick et al. |
| 5,116,753 | 5/1992 | Beattie et al. |
| 5,158,881 | 10/1992 | Aebischer et al. |
| 5,182,111 | 1/1993 | Aebischer et al. |
| 5,209,850 | 5/1993 | Abayasekara et al. |
| 5,284,761 | 2/1994 | Aebischer et al. |
| 5,314,471 | 5/1994 | Brauker et al. |
| 5,344,454 | 9/1994 | Clarke et al. |
| 5,345,587 | 9/1994 | Abayasekara |
| 5,352,511 | 10/1994 | Abayasekara et al. |
| 5,418,154 | 5/1995 | Aebischer et al. |
| 5,453,278 | 9/1995 | Chan et al. |
| 5,773,286 | 6/1998 | Dionne et al. |
| 5,786,216 | 7/1998 | Dionne et al. |

OTHER PUBLICATIONS

Tze, et al., "Implantable artificial endocrine pancreas unit used to restore normoglycemia in the diabetic rat," *Nature*, vol. 264, pp. 466–467, Dec. 1976.

Sun, et al., The Use, in Diabetic Rats and Monkeys, of Artificial Capillary Units Containg Cultured Islets of Langerhans (Artificial Endocrine Pancreas) *Diabetes*, vol. 26, pp. 1136–1139, Dec. 1977.

Scharp, et al., "Islet Immuno–isolation: The Use of Hybrid Artificial Organs to Prevent Islet Tissue Rejection," *World J. Surg.*, 8:221–229, 1984.

Guenard, et al., "Influence of Surface Texture of Polymeric Sheets on Peripheral Nerve Regeneration In A Two–Compartment Guidance System," *Biomaterials*, 12:259–263, 1991.

Jager et al., "Repair of the Blood–Brain Barrier Following Implantation of Polymer Capsules," *Brain Research*, 551:163–170, 1991.

Jager et al., "Polymer Encapsulated Dopaminergic Cell Lines As Alternative Neural Grafts," *Prog. Brain Res.*, 82:41–46, 1990.

Dinsmoor, "Miracle Membranes," *Countdown*, 13:34–39, 1992.

Sullivan, et al., "Biohybrid Artificial Pancreas: Long–Term Implantation Studies in Diabetic, Pancreatectomized Dogs," *Science* 252:718–721, May 1991.

Colton, et al., "Bioengineering in Development of the Hybrid Artificial Pancreas," *J. Biomech. Eng.*, 113:152–170, 1991.

Lacy, et al., "Maintenance of Normoglycemia in Diabetic Mice by Subcutaneous Xenografts of Encapsulated Islets," *Science* 254:1782–1784, 1991.

Dionne, et al., "Effects of Hypoxia on Insulin Secretion by Isolated Rat and Canine Islets of Langerhans," *Diabetes*, 42:12–20, 1993.

Jauregui, et al., "Hybrid Artificial Liver," in *Biocompatible Polymers, Metals and Other Composites*, Szycher, M. (ed)., Lancaster, PA Technomic Pub., 1983, 907–928.

Aebischer, et al. "Transplantation of Polymer Encapsulated Neurotransmitter Secreting Cells: Effect of the Encapsulation Technique," *J.Biomech. Eng.*, 113:178–183, 1991.

Guenard, et al., "Syngeneic Schwann Cells Derived From Adult Nerves Seeded in Semipermeable Guidance Channels Enhance Peripheeral Nerve Regeneration," *J. Nueroscience*, 12:3310–3320, 1992.

Ohgawara, et al., "Successful Implantation of Cultured Allo–And Xenograft Islets With The Use of A Diffusion Chamber," *Life Support Systems*, 3 Suppl 1: 645–648, 1995.

Calafore, et al., "Vascular Graft of Microencapsulated Human Pancreatic Islets In Non–immunosuppressed Diabetic Recipients: Preliminary Results," *Diab. Nutr. Metab.*, 4:45–48 Feb. 1991.

Huges, et al., "Engineering of Glucose–stimulated Insulin Secretion and Biosynthesis in Non–islet Cells," *Proc. Natl. Acad. Sci., U.S.A.*, 89:688–692, Jan. 1992.

Lienhard, et al., "How Cells Absorb Glucose," *Scientific American*, Jan. 1992, pp. 34–39.

Monaco, et al., "Transplantation of Islet Allografts and Xenografts in Totally Pancreatectomized Diabetic Dogs Using the Hybrid Artificial Pancreas," *Ann. Surg.*, 214:3398–362 Sep. 1991.

Reach, "Artificial and Bioartificial Replacement of the Endocrine Pancreas," *Artificial Organs*, 16:61–70, 1992.

Schrezenmeir, et al., "The Role of Oxygen Supply in Islet Transplantation," *Transplantation Proceedings*, 24:2925–2929, Dec. 1992.

Selam, et al., "Devices for Insulin Administration," *Diabetes Care*, 13:955–979, Sep., 1990.

Theodorou, et al., "An Assessment of Diffusion Chambers For Use in Pancreatic Islet Cell Transplantation," *Transplantation*, 27:350–353, 1978.

Tresco, et al., "Polymer Encapsulated Neurotransmitter Secreting Cells: Potential Treatment For Parkinson's Disease," *ASAIO J.*, 38:17–23, 1992.

Kanazawa et al., "Development of a Hydrophilic PTFE Porous Membrane Filter," *Sumitomo Denki*, No. 147, pp. 90–95 (Sep. 1995) (translation from Japanese).

CELL ENCAPSULATION DEVICE

This application is a continuation of application Ser. No. 08/532,925, filed Sep. 22, 1995, abandoned.

FIELD OF THE INVENTION

The present invention relates to devices used to encapsulate living cells, and particularly cell encapsulation devices designed to maintain the viability of cells placed therein.

BACKGROUND OF THE INVENTION

Various cell encapsulation devices have been disclosed over the years. The devices are often used to provide therapeutical substances to a recipient or as bioreactors. These devices commonly comprise one of two forms: microencapsulation devices or macroencapsulation devices.

In a microencapsulation device, small quantities of cells are usually suspended in a droplet and enclosed in a semi-permeable membrane. The semi-permeable membrane allows nutrients, waste products, and therapeutic agents, for example, to diffuse across the membrane, while preventing cells and antibodies, for example, from migrating across the membrane. In order to provide enough cells to effect the desired result, microencapsulation devices are usually used in large numbers.

One common limitation of microencapsulation devices is instability of the microcapsule membrane once implanted in a recipient or placed in a bioreactor. Such instability often leads to cell death or inconsistent release of therapeutic agents. As a result, more than one administration of the microcapsules may be required.

A further limitation with many such devices is the possibility of an immunogenic reaction by a recipient to the composition used to make the semi-permeable membrane of the device. This can lead to serious illness in a recipient and/or damage to the device.

Still another limitation is the difficulty of retrieving the microcapsules from either a recipient or a bioreactor.

Representative examples of microencapsulation devices include, but are not limited to, U.S. Pat. Nos. 5,182,111, 5,283,187, and 5,389,535, all issued to Aebischer et al., U.S. Pat. Nos. 4,487,758, 4,673,566, 4,689,293, 4,806,355, and 4,897,758, each issued to Goosen et al., U.S. Pat. No. 4,803,168, issued to Jarvis, Jr., U.S. Pat. Nos. 4,352,883 and 4,391,909, both issued to Lim, U.S. Pat. No. 4,298,002, issued to Ronel et al., and U.S. Pat. No. 4,353,888, issued to Sefton.

In a macroencapsulation device, larger numbers of cells are enclosed in a chamber of some type. These devices have at least one semi-permeable membrane to allow the necessary flow of fluids while safely retaining the cells. Representative examples of macroencapsulation devices include, but are not limited to, U.S. Pat. No. 5,262,055, issued to Bae et al., U.S. Pat. No. 4,911,717, issued to Gaskill, III, U.S. Pat. No. 4,298,002, issued to Ronel et al., U.S. Pat. No. 5,387,237, issued to Fournier et al., PCT/AU90/00281, filed by Baxter International, Inc., U.S. Pat. No. 5,413,471, issued to Brauker et al., U.S. Pat. No. 5,344,454, issued to Clarke et al., U.S. Pat. No. 5,002,661, issued to Chick et al., and PCT/US94/07190, filed by W.L. Gore & Associates, Inc.

Of particular interest is the macroencapsulation device disclosed in PCT/US94/07190, filed by W.L. Gore & Associates, Inc., which is incorporated herein by reference (hereinafter "Gore device"). The Gore device is preferably a cell encapsulation device that is generally cylindrical in geometry with a flexible cell-displacing core enclosed in a selectively permeable membrane. The selectively permeable membrane contains cells within the device while permitting exchange of biochemical substances between the encapsulated cells and the exterior surface of the device. In a situation where the cell encapsulation device is embedded in a recipient and contains allogeneic or xenogeneic cells, the selectively permeable membrane also serves to isolate the encapsulated cells from the immune system of the recipient. The selective permeability of the membrane can be adjusted by impregnating the membrane with an appropriate hydrogel material. The cell displacing core positions the encapsulated cells near the selectively permeable membrane. In this way, the core positions the encapsulated cells in the device at a distance from a nutrient source and at a cell density that minimizes the diffusion distance biochemical substances must traverse between each encapsulated cell and the external environment of the device. This configuration enables a maximum number of encapsulated cells to be maintained in a given volume at high levels of viability and productivity. During assembly of the device, cells are introduced into the device as a suspension through an open end of the device. The open end is then sealed.

In the biotechnology and pharmaceutical industries, for example, there is a need to quickly and easily screen putative therapeutic agents produced by cells for toxicity, bioactivity, and efficacy, and other factors. Conventional techniques for screening therapeutic agents produced by cells include culturing the cells in vitro until sufficient quantities of cells are obtained to produce enough of the therapeutic agent for screening. Once the desired population of cells is established, the cells are allowed to secrete their products into the culture medium until sufficient amounts of the therapeutic agent are produced. The culture medium containing the putative therapeutic agent is then separated from the cells and concentrated, if necessary. The putative therapeutic agent is usually purified from the culture medium before screening. The purified agent is then screened in vitro and/or in vivo. This is often a laborious, expensive, and time consuming process.

A device and method that eliminates some of the steps of conventional screening techniques would be useful. Though the Gore device, supra, is particularly suited for this type of screening, further improvements are believed possible in the device.

One method to eliminate some steps in screening putative therapeutic agents would be to implant a cell encapsulation device of the present invention, containing cells that produce the putative therapeutic agent, into a test subject.

Once the cell encapsulation device is implanted in a test subject, the putative therapeutic agent would be delivered to the subject directly, eliminating the need to separate the cells from a culture medium and to concentrate, purify, and deliver the agent. Various assays for the putative agent could be performed on the test subject or on samples taken from the subject in order to evaluate the therapeutic agent.

In the field of gene therapy, for example, one method to effect a desired therapy is to harvest certain cells from a patient or donor and genetically manipulate the cells ex vivo to express a desired gene product. The gene product is often a substance needed by the patient, but not produced, or improperly produced, by the patient's own cells. Once the cells have been genetically engineered to produce the desired gene product, the cells are introduced directly into the patient with the intent that the cells will survive in the patient and produce the gene product in amounts and for a length of time sufficient to correct or ameliorate the gene product deficiency in the patient. Since the genetically engineered cells are introduced directly into the patient, the cells are essentially free to move and migrate throughout the patient's body. This is a serious concern because the genetically engineered cells are often transformed and contain oncogenes. The presence of such motile transformed cells in a patient often presents an unacceptable safety risk to the patient.

An implantable cell encapsulation device that prevents genetically engineered cells from contacting a patient's cells and migrating through the patient's tissues while delivering a therapeutic gene product to the patient from the encapsulated cells would be useful in the field of gene therapy.

SUMMARY OF THE INVENTION

The present invention is an improved cell encapsulation device for containing and maintaining the viability of living cells. While the device of the present invention has wide applications, it is particularly suitable for permitting the ready testing of putative therapeutic substances, or agents, produced by the cells. The device is also particularly suitable for containing genetically engineered cells while permitting a desired gene product produced by the encapsulated cells to be delivered from the cells to a patient or a tissue culture. One embodiment of the present invention comprises: a selectively permeable cover comprising a microporous material; a core within the cover, the core preferably comprising a swellable material that expands from an initial first radial dimension to an enlarged second radial dimension upon exposure to an aqueous solution; at least one opening within the cover; a cell delivery device to transfer cells into the device through the opening; and means to seal the opening following introduction of cells into the device.

This construct allows for the quick and easy introduction of cells into the device, with minimal shear force applied to the cells, with the preferred swellable core gradually positioning the cells into a correct operative position following introduction of cells into the device. Ideally, the means to seal the device actuates automatically once the device has been filled with cells and the cell delivery device removed.

In a still further preferred embodiment of the present invention, the cell encapsulation device includes an outer cover that is sufficiently water permeable to allow for ready separation of cells and water upon introduction of suspended cells into the device under relatively low pressures. This allows for easy concentration of cells in the device without pre-concentrating the cells.

BRIEF DESCRIPTION OF THE DRAWINGS

FIG. 4 also illustrates the portion of the device containing spacer 48, sealing means 46, along with the accompanying portion of cover 42, and the accompanying portion of core 41 having been removed from the device.

DETAILED DESCRIPTION OF THE INVENTION

Figure 1:
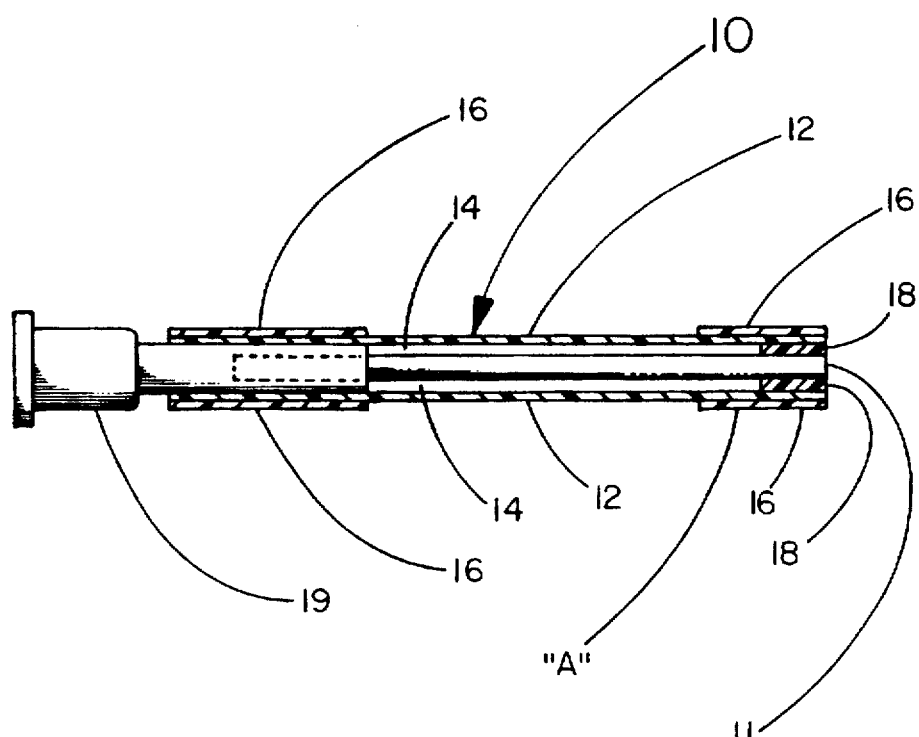
FIG. 1 illustrates a cross-section of the device 10 of the present invention having a core 11 within a cover 12 sealed against an optional spacer 18 with sealing means 16. The optional spacer 18 is placed over the core 11 to facilitate sealing the device. The space between the cover 12 and the core 11 is referred to as a cell zone 14 for containing cells. A cell delivery device 19 is also illustrated in FIG. 1. Point "A" in FIG. 1 shows the general area in which a cut is optionally made in the device 10 to remove the portion of the device containing the spacer 18, along with the accompanying portion of cover 12, and the accompanying portion of core 11.

Referring to FIG. 1, the device 10 of the present invention comprises a core 11 within a cover 12 that is sealed with sealing means 16. An open space in between the core and the cover is a cell zone 14 capable of containing cells. A spacer 18 is optionally provided to assist in maintaining the dimensions of cell zone 14 and to facilitate sealing of the device. In addition, a cell delivery device 19 is provided as a component of the device. Upon removal of the cell delivery device 19 from within cell zone 14, sealing means 16 constricts to seal the device and encapsulate cells contained therein.

The present invention is directed to a cell encapsulation device for use either in vivo or in vitro. When used in vivo, for example, the present invention can deliver therapeutic substances to a recipient from cells encapsulated in a device implanted in the recipient. The therapeutic substance can be derived from cells that are similar to cells absent or diseased in the recipient. Alternatively, the therapeutic substance can be derived from cells genetically engineered to produce gene products that are absent or improperly produced by the recipient's own cells.

For in vitro use, the present invention with a cache of cells encapsulated in the device can operate as a bioreactor, for example.

The device of the present invention is particularly suited for screening putative therapeutic substances or therapeutic agents produced by cells. Cell lines that produce therapeutic substances or agents can also be screened with the device. Screening can be conducted either in vivo or in vitro.

As described above, production and screening of putative therapeutic substances and agents is often an involved and expensive process. In performing a screening procedure for a putative therapeutic substance or agent with the present invention, the substance or agent being screened is delivered from the cells encapsulated in the device across the permeable cover of the device directly to a test subject or tissue culture. By using the present invention to screen putative therapeutic substances and agents, it is unnecessary to separate cells from a culture media and to concentrate, purify, and administer the putative therapeutic substance or agent in order to perform the screening procedure.

In practice, a cell encapsulation device of the present invention permits a user to quickly, easily, and gently transfer a desired quantity of cells into the cell zone of the device without having to pre-concentrate the cells. The cover of the device is made of a material that is impermeable to cells, while being permeable to fluids. As an aqueous cell suspension is instilled into the cell zone of the device, cells are retained in the cell zone by the cover and excess fluid from the cell suspension flows through the cover of the device. This filtration of cells by the cover of the device continues until a desired number of cells have been placed in the cell zone. In a preferred embodiment, the cover of the device is spontaneously wettable with liquid water and so is instantaneously ready to filter a cell suspension as the suspension is placed in the device. In this embodiment, as the normally opaque cover is wetted with liquid water, it becomes essentially translucent to transparent. The essentially translucent to transparent cover enables a user to see into the cell zone and observe and monitor the loading of cells into the device, and the growth or condition of cells in the device during use.

Cells are transferred to the cell zone of the device through a cell delivery device, such as a blunt-end stainless steel syringe needle, from a syringe. Other containment and delivery devices are also suitable cell delivery devices for use in the present invention, including, tissue culture pipettes, tubing leading from cell culture pumping devices, tubing leading from gravity fed cell culture containers, etc. Additionally, through use of a full or partial vacuum established in the cell encapsulation device of the present invention, it may be possible to draw a cell suspension into the device.

Once the cell zone has been loaded with the desired number of cells, the cell delivery device is removed from the cell encapsulation device. As the cell delivery device is removed, sealing means are actuated to constrict and seal the end of the device encapsulating the cells contained therein. In the preferred embodiment, the sealing means closes the opening automatically upon filling of the device and/or removal of the cell delivery device.

Preferably, the device of the present invention has a core that maintains encapsulated cells up against or near the cover where the diffusion distances between the cells and an external nutrient source are minimized. The core may be made of either a swellable or non-swellable material. A swellable core and especially a water swellable core is preferred. A water swellable core made of a hydrogel material is most preferred because the hydrogel material can be initially dehydrated to decrease the size of the core and subsequently rehydrated to increase the size of the core. A dehydrated water swellable core in the device creates a larger volume in the cell zone than a non-dehydrated water swellable core of the same materials and initial dimensions. As a result, cells can travel more easily through the larger cell zone as the device is loaded with cells. When loaded with cells, the clearance between the outer surface of the core and the inner surface of the cover of the present invention must often be small, however. This is due to the need to minimize the diffusion distance between the cells encapsulated in the device and an external nutrient source in order to maintain the viability of the cells. To obtain the requisite clearances between the core and the cover, the dehydrated water swellable core is rehydrated and swollen to a predetermined size during and/or after loading of the cells into the cell zone. In this way, a dehydrated water swellable core initially provides a larger cell zone so cells can travel more easily through the cell zone as the device is loaded with cells and subsequently provides correct positioning of cells in the device and the often needed small clearances for the cells between the core and the cover.

In a preferred embodiment, a dehydrated water swellable core is rehydrated by the aqueous portion of a cell suspension as the suspension is loaded into the cell zone. As the core becomes rehydrated, it swells to size during and after the cells are loaded into the device. Other means to provide a swellable core may include an inflatable core that is inflated after cell installation through use of gas or liquid, a core that is mechanically enlarged following cell installation, such as by diametric recovery after axial stretching, a polymer core that is expanded using expandable microspheres, or the like, etc. It should be appreciated that similar results may likewise be achieved by providing a cover that is constricted down in circumference after cell installation.

Construction and assembly of the components of the device of the present invention is described as follows.

As mentioned above, the core of the present invention can be made of either a swellable material or a non-swellable material. Non-swellable cores may be formed from any suitable biocompatible material, including polytetrafluoroethylene, poly(dimethyl siloxane) rubber, polyurethane, polyethylene, polyethylene vinyl acetate, polypropylene, polybutadiene, polyvinyl chloride, polyvinyl acetate, polyacrylonitrile, polyamide, glass or glass fibers, stainless steel, and other materials known to those skilled in the art. Poly(dimethyl siloxane) rubber is preferred.

The preferred core is made of swellable polymers. Examples of swellable polymers suitable for making the core may be selected from the group consisting of hydrophilic polyacylonitrile such as HYPAN® Structural Hydrogel (Hymedix International, Inc., Dayton, N.J.), chitin, chitosan, hydroxyethylmethacrylate (HEMA), hydrophilic polyurethane, polyethylene glycol, polyacrylamide, polyacrylic acid, and silica gel, or hydrogels derived from polysaccharides, such as alginate and other materials known to those skilled in the art. The core is preferably a flexible polymer or elastomer or blends with copolymers of swellable and non-swellable materials. More preferably, the core may be manufactured from polysaccharides, hydrophilic copolymers of polyacrylonitrile, or other polymer components. Core compositions such as HYPAN® Structural Hydrogel comprising a copolymer of polyacrylonitrile and acrylamide are most preferred.

When a hydrogel, such as HYPAN® Structural Hydrogel, is used to make the core component of the present invention, the water content of the hydrated gel should be sufficient to provide flexibility while not exceeding a water content that forms pores sufficiently large to allow cells to enter the core. Preferably, the gel comprising the core is hydrated to between about 35% and about 95%. Most preferably, the water content is about 80%.

Figure 6:
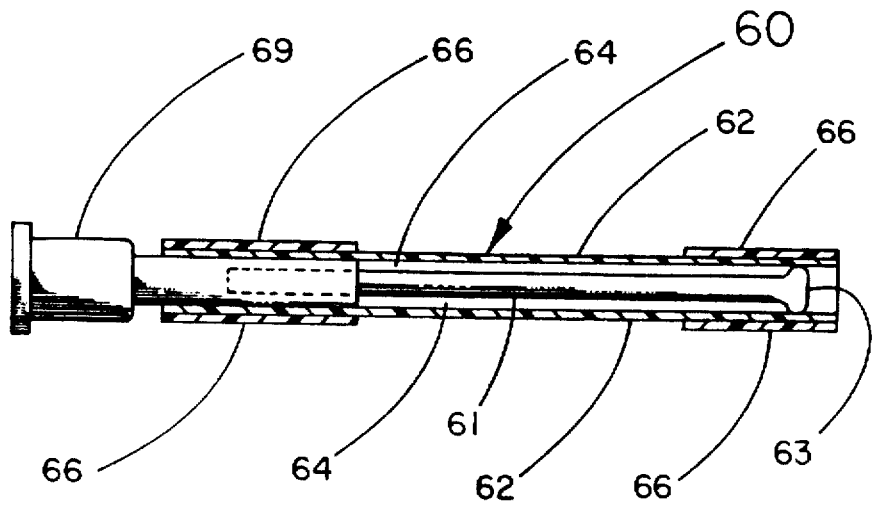
FIG. 6 illustrates a cross-section of the present invention 60 with a core 61 having an integral spacer 63 comprising additional material at one end of the core to replace or supplement the separate spacer 18 shown in FIG. 1. Cover 62, cell zone 64, sealing means 66, cell delivery device 69 are also depicted in the Figure.
Figure 7:
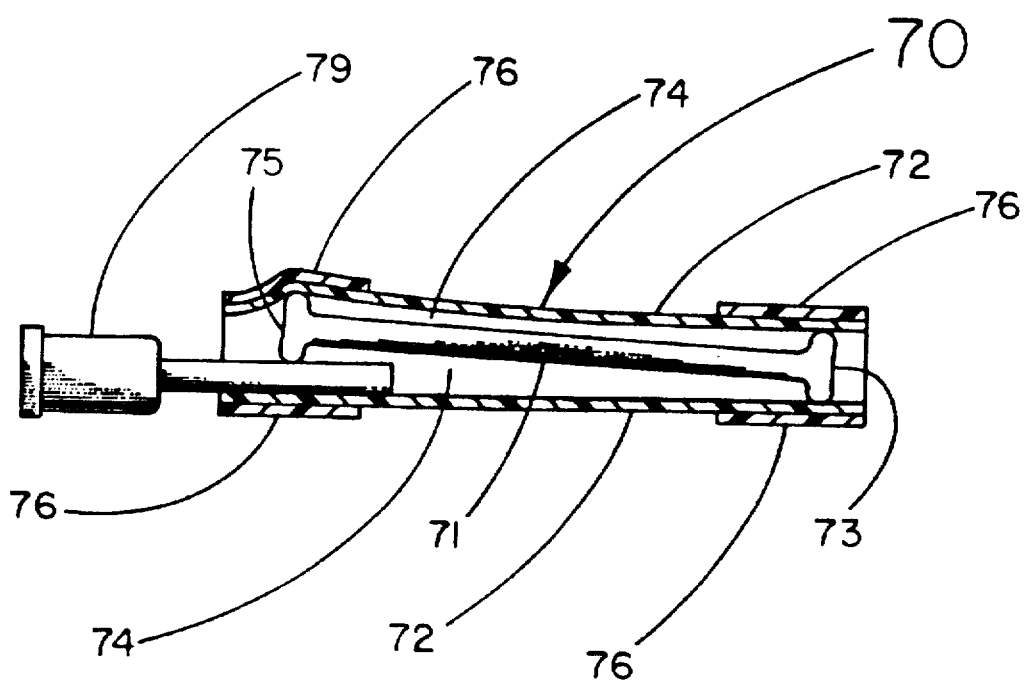
FIG. 7 illustrates a cross-section of the present invention 70 with a core 71 having integral spacers 73 and 75 at each end of the core to replace or supplement the spacer 18 shown in FIG. 1. In this embodiment, a cell delivery device 79 is placed adjacent to core 71 and held in place with sealing means 76. Cover 72, cell zone 74, and cell delivery device 79 are also depicted in the Figure.

The core is preferably formed as a generally cylindrical rod by extruding the polymer through a round die. For a core made of swellable materials in particular, the shape of the core can be varied to take advantage of the increase in size of the core when the core has been swollen. Referring to FIGS. 6 and 7, for example, a swellable core can be made to have additional swellable material at one or both ends of the core. The additional swellable material serves initially as a spacer to assist in maintaining the dimensions of the cell zone and ultimately as part of the means to seal the cover to the core.

For a water swellable core, the core material is preferably substantially dehydrated, or only partially hydrated, prior to assembly of the device. Preferably, the water swellable core is dried under restraint to provide a stiffened substantially straight rod form. The water swellable core becomes rehydrated and swells when an aqueous solution is placed in contact with the core. Preferably, the water swellable core is in the device when it is rehydrated. When rehydrated, the water swellable core preferably swells primarily in the radial direction only. In this way, the water swellable core has an initial first radial dimension in its dehydrated state that is enlarged by swelling to a second radial dimension upon exposure of the core to an aqueous solution. In a preferred embodiment, the water swellable core material has a first radial dimension that is at least 50% of the second radial dimension.

Optionally, a sheath having the desired second radial dimension for the core can be placed over a dehydrated core prior to rehydration. When the core is rehydrated, the sheath restricts the swollen core to the radial dimension of the sheath. A sheath surrounding a swollen core enables a cell zone to be formed within the cover having more precise and consistent dimensions. Suitable material for the sheath include, but are not limited to, polytetrafluoroethlyene, expanded polytetrafluoroethylene, woven or microporous Dacron® polyester, woven nylon, microporous polycarbonate, woven polyacrylonitrile, Mylar®, polyethylene, polypropylene, and polysulfone, either alone or in combination.

Preferably, the aqueous solution used to rehydrate the water swellable core also contains the cells to be placed in the device. In this way, as the device is loaded with cells, the water swellable core is rehydrated and swells to operative size in the device. This results in optimal positioning and concentration of cells in the device.

General information concerning the manufacture and handling of hydrogel devices is found in the art, such as in PCT/US94/07190, to W.L. Gore & Associates, Inc., and U.S. Pat. Nos. 4,379,874, 4,420,589, and 4,943,618, each of which is incorporated herein by reference.

The selectively permeable cover component of the present invention is made of a microporous material. There is at least one opening in the cover. Examples of microporous polymeric materials that are suitable for use in making the cover include, but are not limited to: expanded polytetrafluoroethylene (ePTFE); woven/and or non-woven polymers such as polyester, polyethylene terephthalate, polyamide, vinyl acetates, polypropylene, polyethylene, polyacrylonitrile, polyaramide, polyhydroxy acids (such as polylactic acid, polyglycolic acid, or polycaprolactone); open cellular foams such as phenolic and epoxy resins, polyurethanes, chloroprene, isoprene, polyethylene, polypropylene, polystyrene, polyvinyl chloride, latex foam rubber, polyurea-formaldehyde, polyhydroxy acids (such as polylactic acid, polyglycolic acid, polyhydroxybutyric acid, polyhydroxyvaleric acid, or polycapralactone); and poromerics and/or permeable matrix membranes (such as polyvinyls, polyamide, polyimide, polyacrylonitrile, polysulfone, polyvinylidene fluoride, polypropylene, polymethylmethacrylate, polycarbonate, regenerated cellulose, or cellulose acetate). These materials are most useful for constructing the cover of the present invention when in the form of films, tapes, sheets, or tubes, for example. The most preferred microporous polymeric film material is ePTFE. Biocompatible microporous metal may also be suitable for making the cover, either alone or in combination, with microporous polymeric materials and/or surfactants or wetting agents.

Expanded PTFE, or ePTFE, is characterized primarily by a multiplicity of open, interconnecting voids defined by nodes and fibrils, high tensile strength, resistance to biological fouling, and stable chemical properties. Expanded PTFE materials, including ePTFE films, may be made according to the teachings of U.S. Pat. Nos. 3,953,566, 3,962,153, 4,096,227, 4,187,390, and 4,902,423, each of which is incorporated herein by reference. Expanded PTFE films suitable for use in the present invention can have fibrils oriented primarily in a single direction, in two directions, or in more than two directions. These films are commonly referred to as uniaxially, biaxially, or multiaxially oriented materials, respectively.

Though the cover can be made of at least one layer of a thin tape of microporous polymeric material, such as ePTFE, the tensile strength and dimensional stability of the microporous polymeric membrane can be varied by incorporating one or more fabrication techniques known to produce thin, high tensile strength reinforcing films. These techniques include, but are not limited to, weaving or knitting of filaments, web drawing of porous films, and lamination, for example.

A cover of the present invention is able to be configured in a variety of useful shapes, including, but not limited to, tubes, planar sheets or tapes, and capsules, for example. Lamination of a microporous polymeric film material of the present invention is a preferred method for producing a variety of shapes. For example, thin, highly oriented fibers or bands of microporous polymeric film can be laminated to create surfaces of varying curvature and flexibility.

Preferably, a cover of the present invention comprises an ePTFE material in the form of a laminate of two or more layers of film oriented in different directions. This ePTFE laminate has a thickness less than about 100 microns, preferably less than about 50 microns, most preferably less than about 5 microns.

The term "lamination" is intended to refer to the assembly of two or more microporous polymeric film layers into close approximation such that the surface of one layer is nearby and in parallel orientation with the surface of the other layer. The surface of a polymeric film layer is considered to be nearby the surface of an adjacent parallel film layer if it is within ten times the nominal film unit thickness of the microporous polymeric film comprising the laminate. Lamination of microporous polymeric films can be performed using the microporous polymeric film alone or in combination with an adhesive.

Laminations performed with the microporous polymeric film alone may be accomplished through bonding with heat or a solvent. The result is a microporous polymeric film laminate bound to the adjacent film layer by homogeneous interaction. Homogeneous interactions include, but not be limited to, the creation of crystalline binding domains, glassy amorphous domains, ionic bonds, hydrogen bonds, or covalent cross-links.

Alternatively, an adhesive may be used to bind adjacent layers of a microporous polymeric film together, provided that the effect of the adhesive is substantially limited to the creation of fastening domains between the film layers and does not cause excessive fouling of the laminated film. Excessive fouling of the laminated film results when more than about 70% of the available continuous passages in the microporous polymeric film are occluded. Suitable adhesives for use in the present invention include, but are not limited to, polyurethane, polyester, and fluorinated ethylene propylene, polyurea, polycarbonate, and polyepoxides, either alone or in combination. Adhesive materials employing solvents can also be used either alone or in combination with the above-listed materials to adhere layers of a microporous polymeric film together.

To form a laminated ePTFE cover of the present invention, a microporous polytetrafluoroethylene film component is first obtained. One such film, having a thickness of about 25 microns, is a porous expanded polytetrafluoroethylene film made according to the teachings of U.S. Pat. Nos. 3,953,566, 3,962,153, 4,096,227, 4,187,390, and 4,902,423, each of which is incorporated herein by reference. The microporous expanded polytetrafluoroethylene film has a void volume greater than about 40%, preferably greater than about 75%, and most preferably greater than about 85%, as measured by comparing the apparent bulk density of the microporous expanded polytetrafluoroethylene film with a full density, or non-porous, polytetrafluoroethylene film. The void volume is primarily comprised of passages, pores, or spaces coursing through the film.

The passages range in diameter, or minimum dimension, orthogonal to the direction of solute flow through the pore from about 0.02 microns to about 100 microns. Alternatively, the diameter of a pore can be determined by the largest spherical particle that can pass through the pore. The passages often interconnect within the film. Passages that traverse the thickness of the film and open onto both surfaces of the film form continuous passages through the film. Use herein of the term "passages" in reference to a microporous polymeric film is intended to include both continuous and non-continuous passages in a particular microporous polymeric film or laminate.

The void volume is related to the porosity of the microporous polytetrafluoroethylene film. The porosity value represents the space in the microporous film that does not contain film material, (i.e., that portion of the film that comprises pores, usually unless the pores have been filled with some other material (e.g., water)). Expressed as a percentage, the porosity value measures the percent (%) volume of the microporous film that is not occupied by microporous material. To derive the porosity value, in percent, for microporous polymeric film, the following formula is generally used:

Porosity=$100(1-(\rho_a/\rho_f))$ where:

$\rho_f$ is the density of the polymer material constituting the solid phase of the microporous material, and $\rho_a$ is the apparent density of the microporous film material given by the volume occupied by the outer boundary of a representative sample of the microporous material divided by the mass of that material as determined by weighing the material at standard atmospheric conditions.

The porosity value is determined for microporous polymeric films, wherein the void space is empty, that is, has not been filled with any other liquid or solid impregnating material.

Preferably, a laminated microporous polymeric material of the present invention is provided that exhibits tensile strength in several planar directions. For example, the tensile strength of a microporous polymeric film material is commonly greatest in the principal direction of orientation of that film. Such oriented films generally exhibit less tensile strength in a direction orthogonal to the direction of principal orientation of such film, and are thus advantageously placed in a structural composite such that the principal direction of orientation of such film is aligned with the direction of anticipated primary loading. To produce microporous polymeric reinforcing films which feature tensile strength in multiple directions, lamination of two or more layers is accomplished with the film layers oriented in a distributed set of directions. A common two ply lamination would involve lamination of a second layer at a 90° angle (orthogonal) orientation to a first layer. This results in a laminate denoted a 0, 90 laminate. Other common lamination schemes include a three ply lamination such as a 0, 45, 90 laminate or a 0, 60, 120 laminate. A four ply lamination scheme might include a 0, 45, 90, 135 laminate, for example. Such multidirectional lamination schemes result in more distributed mechanical properties and less specific orientation in the final product. Alternatively, biaxially oriented or multiaxially oriented films may be used in the present invention, either alone or in multiple layers.

Microporous ePTFE is a hydrophobic material that normally does not permit liquid water to enter and traverse the void, or porous, spaces and passages of the material. Application of certain alcohols, low surface tension liquids, wetting agents, or surfactants to a microporous ePTFE material, on the other hand, can render the surfaces and the passages of the ePTFE material wettable with liquid water. For covers of the present invention made of a microporous ePTFE material, the normally hydrophobic ePTFE material is rendered hydrophilic and wettable with liquid water using alcohol, wetting agents, or hydrophilic surfactants. Such a wettable ePTFE material permits liquid water to flow along the surfaces of the material and to enter and traverse the pores and passages therein. In the preferred embodiment, the cover is spontaneously wettable with liquid water and is capable of filtering cells from an aqueous suspension.

A method of rendering a cover of the present invention made of ePTFE water wettable with an alcohol is as follows. The cover is immersed in ethanol (i.e., about 70–100%), for example, for a few seconds (i.e., about 1–10 sec.) to coat the surfaces of the material and fill the pores, or void spaces, with the ethanol. The ethanol-saturated ePTFE material is then immersed in distilled, deionized water, or normal saline for a few minutes to displace the ethanol from the surfaces and pores of the ePTFE with the liquid water. While still wet with liquid water, the cover is loaded with cells as described herein below. Although this is an acceptable method for rendering ePTFE wettable with water and for use in the present invention, some potential problems with the method remain. For example, spontaneous dewetting of the ePTFE cover is a problem due to ePTFE's extreme hydrophobicity. In addition, an ePTFE material rendered wettable with alcohol then liquid water can cause air bubbles to form in the device when the device is loaded with an aqueous suspension of cells. This is believed to be due to bubbles forming from air trapped in the void spaces of the material and/or degassing of the aqueous portion of the cell suspension wetting the ePTFE material.

As described in greater detail below, it is desirable for the cover to be essentially translucent to transparent when loading cells into the cell zone of the device. An opaque ePTFE material can be rendered essentially translucent to transparent when wet with liquid water by using wetting agents or surfactants adsorbed onto the surfaces and into the void, or porous, spaces of an ePTFE material. Accordingly, ePTFE materials treated with wetting agents or surfactants are preferred materials for making the cover of the present invention.

The above-described problems associated with ePTFE rendered water wettable with ethanol can be prevented, or minimized, by replacing the distilled or deionized water in the above-described method with a very dilute aqueous solution of a wetting agent, such as polyvinyl alcohol. For example, 0.001% polyvinyl alcohol in saline (w/v) has been found to provide enough wetting agent to the ePTFE material to prevent, or limit, spontaneous dewetting of the material, to prevent, or limit, evolution of air bubbles in a device loaded with cells, and to render the normally opaque ePTFE material essentially translucent to transparent. Suitable wetting agents and/or surfactants for use in this method include, but are not limited to, polyvinyl alcohol, polyethylene glycol, sodium dodecyl sulfate, fluorosurfactants, pluronics, and bile salts in percentages ranging from about 0.001–1.0% Suitable solvents for this method include, but are not limited to, saline, water, and aqueous buffers, for example.

In the preferred embodiment of the present invention, wetting agents and/or surfactants are adsorbed onto the surfaces and into the void spaces, pores, or passages of the ePTFE cover and preferably immobilized in situ in order to make the ePTFE material wettable with liquid water. There are many ways to immobilize wetting agents or surfactants, such as, cross-linking, substrate grafting, plasma immobilization, ionic complexation, and free radical grafting, etc. In one example, cross-linking the adsorbed wetting agent or surfactant on the ePTFE in situ immobilizes the wetting agent or surfactant on the ePTFE material. Certain wetting agents or surfactants can be used that render ePTFE spontaneously and substantially completely liquid water wettable. A spontaneously and substantially completely water wettable ePTFE material permits liquid water to flow along the surface and through the passages of the material by merely contacting the material with liquid water. Suitable wetting agents or surfactants for use in the present invention include, but are not limited, to polyvinyl alcohol, poly(tetrafluoroethylene-co-vinyl alcohol), polyacrylic acid, polyethylenimine, and polyethylene glycol. Wetting agents and/or surfactants are adsorbed in various ways, such as solution, or neat, adsorbtion, vapor deposition, plasma immobilization, and thin film assembly, for example. Preferably, polyvinyl alcohol is adsorbed to ePTFE by adsorbing the polyvinyl alcohol onto the surfaces and into the porous, or void, spaces of the material, followed by immobilization via cross-linking the polyvinyl alcohol to itself with a dialdehyde such as glutaraldehyde.

A cover of the present invention made of water wettable ePTFE is strong enough to withstand hydrostatic pressures sufficient to cause water to be forced through the pores of the material across the thickness of the cover. When water is being forced across the thickness of the cover, the water wettable ePTFE material functions as a filter, or an ultrafilter, depending on the permeability of the material. As water moves, or seeps, across the thickness of the cover, it tends to collect into droplets on the outer surface of the cover. As adjacent droplets grow in size, they merge and run off of the cover. This process is referred to herein as "weeping." Most water wettable covers of the present invention are sufficiently permeable to water for pressurized water to visibly weep from the cover without gross channeling of water.

Ideally, the cover of the present invention is sufficiently water permeable to allow the ready separation of water from cells under relatively low pressure. A ready weep flow of ranging from about 0.01 ml/cm$^2$/minute to about 100 ml/cm$^2$/minute at a pressure ranging from less than about $3.4 \times 10^4$ Pa to about $6.9 \times 10^5$ Pa should permit relatively rapid cell concentration within the device.

This is an extremely beneficial attribute of the present invention. Unlike previous cell containment devices that require cell concentration before insertion of the cells in the cell device and then carefully calculated and controlled transfer, the present invention allows cells to be easily transferred to any desired concentration with minimal pre-concentration steps. Further, by flushing a cell-filled apparatus with clear water after initial loading of the cells, a user can assure that cells are flushed into the device and not left as a wasted residue on the apparatus.

Another benefit of the cover becoming essentially translucent to transparent is that in a translucent or transparent condition, the cells in the device can be observed through the cover both during and after loading of cells. This not only assists in the loading of cells, but also makes monitoring of the cells during use much easier.

The selectively permeable cover should have a pore size range sufficient to prevent cells from moving into or out or the device, but large enough to allow the passage of nutrients, waste products, and therapeutic substances secreted by cells contained within the device. In one embodiment, the characteristic pore size is sufficiently small as to filter or exclude particles on a molecular scale. Such molecular weight cut off (MWCO) properties may be useful for excluding proteins, etc., produced by the immune system of a recipient from traversing the cover and adversely effecting cells encapsulated in the device. The precise MWCO range will vary depending on the membrane material, type of cells contained within the device, the size of the therapeutic cell product to be released into the surrounding environment, and the host environment, etc. Accordingly, selectively permeable covers having a MWCO of between about 10 kD to about 2000 kD may be suitable for use in the present invention. A MWCO range of between about 30 kD and 500 kD is particularly preferred in applications where it is desired to isolate the contained cells from contact with molecules of the immune system capable of recognizing or destroying the contained cells.

Referring to FIG. 1, a preferred method of assembling a device of the present invention is as follows. A substantially dehydrated, or only partially hydrated, core 11 and a selectively permeable cover 12 in a tubular form are separately prepared. The cover 12 has an opening at each end. The core 11 is placed inside the cover 12 and retained therein with sealing means 16 in a substantially dehydrated or only partially hydrated state until the cell zone 14 is loaded with an aqueous suspension of cells.

Prior to placing the core 11 inside cover 12, a spacer 18, preferably in the form of a ring, is optionally placed over one end of the core 22. The luminal surface of the spacer 28 is preferably shaped to conform to the shape of the outer surface of the core 11. The outer surface of the spacer 18 is preferably shaped to conform to the luminal surface of the cover 12.

The spacer 18 serves different functions in the present invention, depending on whether the core 11 is made of a non-swellable polymer or a swellable polymer. For a core 11 made of a non-swellable polymer, the spacer 18 maintains the radial dimension of the cell zone 14 to the end of the device, while providing a structure against which sealing means 16 operates to constrict and seal cover 12. For a core made of a swellable polymer, the spacer 18 maintains sealing means 16 in a stretched conformation until the swellable core is rehydrated and swells from a first radial dimension to a second radial dimension. Once the swellable core is rehydrated and swollen, the portion of the device containing the spacer is preferably removed. Removal of this portion of the device is conveniently accomplished with a sharpened edge, such as a scalpel blade, at point "A" in FIG. 1, for example. Point "A" in FIG. 1 shows the general area in which a cut is optionally made in the device 10 to remove the portion of the device containing the spacer 18, along with the accompanying portion of cover 12, and the accompanying portion of core 11.

Figure 4:
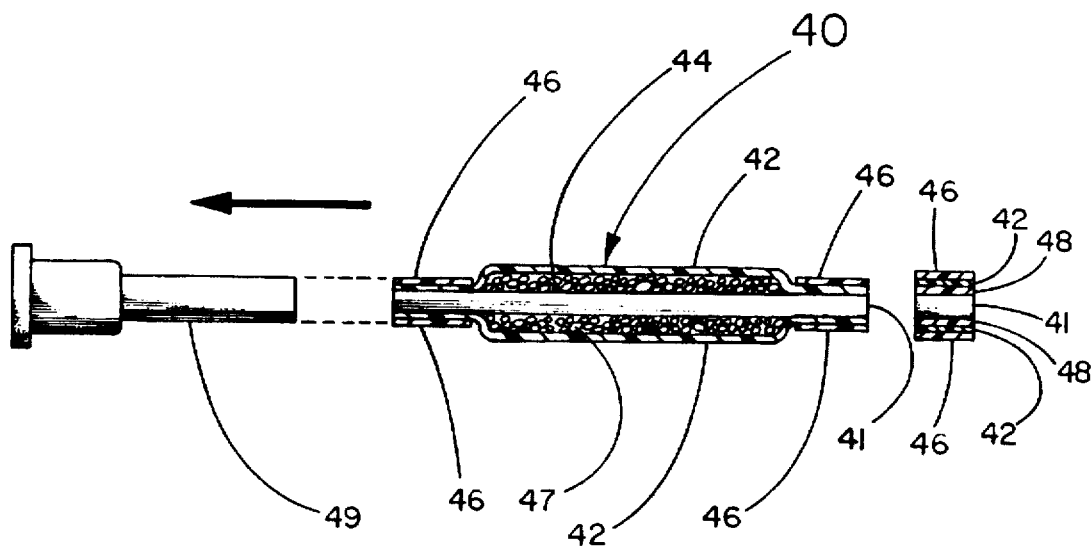
FIG. 4 illustrates the device assembly of FIG. 1 with cell zone 44 between core 41 and cover 42 loaded with cells 47, sealed with sealing means 46, and separated from the cell delivery device 49.

Once the portion of the device containing the spacer is removed, sealing means 16 constrict to seal cover 12 against swollen core 11 (See FIG. 4, for example). It should be understood, however, that removal of the portion of the device containing the spacer 18 is not required in order for the device to be sealed, if the sealing means provide a fluid-tight fit between the outer surface of swollen core 11 and the inner surface of the spacer 18.

Once the spacer 18 is applied to core 1, the core is inserted inside cover 12 as shown in FIG. 1. Sealing means 16, such as a constriction device, is then placed over cover 12 to compress the cover against the spacer 18, thereby securing the core 11 to the end of cover 12. If the spacer 18 is not applied to core 11, the core 11 is inserted inside cover 12 and sealing means 16 placed over cover 12 and allowed to constrict cover 12 against core 11, thereby securing the core 11 to the end of the device 10 and sealing the end as well.

Suitable materials for the spacer 18 include, but are not limited to, polytetrafluoroethylene, polypropylene, polyethylene, poly(dimethyl siloxane) rubber, viton, buton, and elastomers, hydrogel materials, such as, HYPAN® Structural Hydrogels (Hymedix International, Inc., Dayton, N.J.), hydroxyethylmethacrylate, and polyvinyl acetate, biocompatible metals, such as, stainless steel and titanium, for example.

As illustrated in FIGS. 6 and 7, the spacer can optionally be replaced, or reduced in size, with additional core material on one or both ends of the core. Assembly of a device of the present invention with a core as illustrated in FIG. 6 is similar to the assembly of a device having a spacer at one end of the core.

Figure 2:
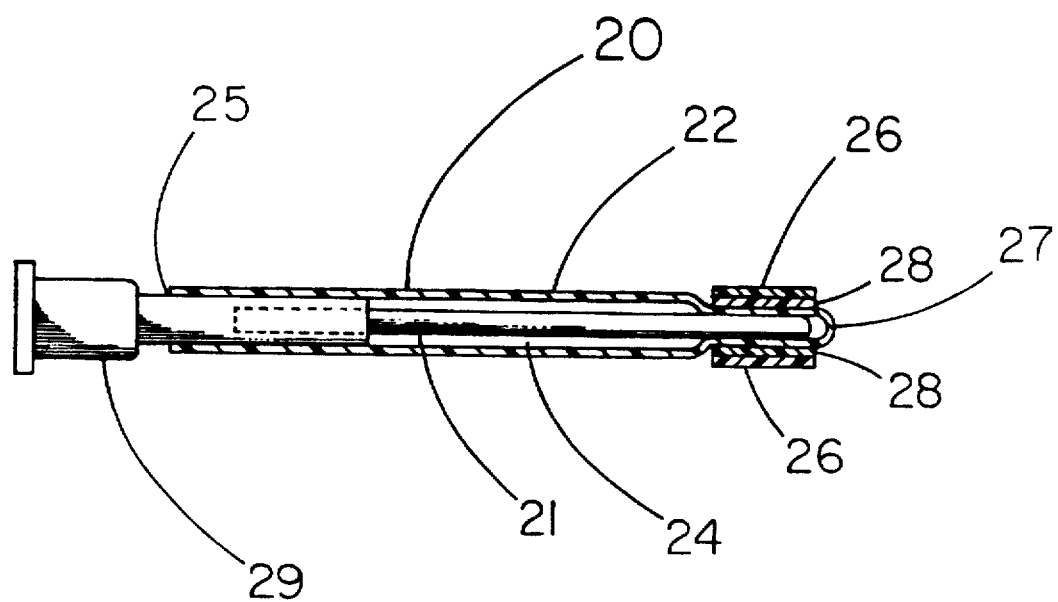
FIG. 2 illustrates a cross-section of the present invention 20 with a cover 22 having one open end 25 and one closed end 27. The cover 22 defines a cell zone 24 between cover 22 and core 21. The core 21 is secured in the closed end of the device with sealing means 26. A cell delivery device 29 is included as a component of the device.

A cover having only one open end is treated similarly to a cover having two open ends, except that the core, optionally having a spacer in place or additional core material on one end of the core, is inserted inside the cover through the opening in the device through to the side of the device opposite the opening as illustrated in FIG. 2. A sealing means 26 is placed over cover 22, the optional spacer 28 or additional core material, and the core 21 to compress the cover 22 against the spacer 28 or additional core material, thereby securing the core in the device. Alternatively, the spacer 28 or additional core material can be eliminated and the sealing means 26 used to compress the cover 22 directly against the core 21 to seal the device 20.

Referring to FIG. 1, the remaining open end of the device is assembled with a cell delivery device 19 attached to the cell encapsulation portion of the present invention with a sealing means 16, or a constriction device. Preferably, the cell delivery device 19 is a blunt end syringe needle made of stainless steel, or equivalent material. Other suitable cell delivery devices include, but are not limited to, cannulae, cylindrical tubes, flattened tubes, tissue culture pipettes, tubing leading from cell culture pumping devices, and tubing leading from gravity fed cell culture containers, etc. Suitable materials for making the cell delivery device include, polytetrafluoroethylene, poly(dimethyl siloxane) rubber, polyurethane, polycarbonate, polyethylene, polyethylene vinyl acetate, polysulfone, polypropylene, polybutadiene, polyvinyl chloride, polyvinyl acetate, polyamide, glass or glass fibers, stainless steel, etc.

In embodiments having a core as illustrated in FIGS. 1, 2, and 6, for example, the inner diameter of the cell delivery device should be sufficiently larger than the outer diameter of the core for cells to be introduced into the cell zone of the device without subjecting the cells to shear forces of sufficient magnitude to damage the cells. The outer diameter of the needle should be smaller than the inner diameter of the cover in order for the cover to be placed over the end of the needle.

The unsealed end of the core is placed inside the delivery end of the needle as shown in FIGS. 1, 2, and 6, for example. The unsealed end of the cover is placed over the outside of the delivery end of the needle as shown in FIGS. 1, 2, and 6, for example.

In embodiments having a core as illustrated in FIG. 7, for example, the delivery end of the cell delivery device is placed within the cover and adjacent to the core as shown in FIG. 7.

In the embodiments illustrated in FIGS. 1, 2, 6, and 7, for example, a sealing means is placed over both the cover and the needle end of the cell delivery device thereby attaching the cell encapsulation portion of the device to the cell delivery device. Sealing means preferably comprise a cuff of polymeric material having elastomeric properties. The sealing means are also referred to herein as a "constrictive device."

"Sealing means" as used herein refer to devices or materials that serve to seal the cover to a spacer, or in the absence of a spacer, to the core. Some sealing means provide a circumferential constrictive force to the cover, pressing it against either the spacer or the core. Examples of such sealing means include, but are not limited to, constrictive elastomeric rings, successively wrapped fibers or films, heat activated constrictive tubes, and chemically activated constrictive tubes, for example. Mechanical clamps, such as those based on plastic deformation of a band (i.e., crimping a metal or plastic band), hose clamps, band clamps, tacking, and flat bar clamps are also contemplated sealing means. Other sealing means provide a seal by expanding from within the device outwardly against the cover. For example, a swellable core can swell and expand radially to match the inner dimensions of the cover forming a seal thereby. With this method, it is preferred to reinforce the cover to resist further swelling of the core from inside the device in order to form a seal. A core can be confined, or pre-stressed, to a radial diameter less than the inner diameter of the cover. Once the core is placed inside the cover, the core is released from confinement and allowed to expand tightly against the cover to form an interference seal, or fit. The device of the present invention may also be sealed with an adhesive, heat sealed, ultrasonically sealed, etc.

One method of sealing the device with an adhesive is to immerse an end of the core into the adhesive and to position the adhesive coated end into cover. Finishing steps appropriate for the particular adhesive are then performed to seal the device.

Suitable materials for construction of constrictive devices, or sealing means, include, but are not limited to, poly (dimethyl siloxane) rubber, fluoroelastomers, urethanes, and hydrogels. Poly(dimethyl siloxane) rubber is preferred.

Suitable materials for construction of mechanical clamps include, but are not limited to, stainless steel, titanium, nylon, polysulfone, engineering plastics, and composites thereof.

Suitable adhesives for sealing the device include, but are not limited to, cyanoacrylate, poly(dimethyl siloxane) rubber, urethane, and hydrogels.

Alternatively, sealing means can be comprised of an interpenetrating network of an ePTFE cover material and an elastomeric polymer. For example, uncured poly(dimethyl siloxane) rubber can be applied to the surfaces and impregnated in the void, or porous, spaces of an ePTFE cover material in the areas of the cover to be sealed. Following assembly of the core and the cover as described above, a constrictive device is placed over the areas of the cover having the above-described interpenetrating network. The poly(dimethyl siloxane) rubber is then cured to seal the cover to the core. The constrictive device is usually removed once the seal has been formed. Ideally, this method produces a seal with few, if any, wrinkles in the cover. While probably not critical, wrinkles in the cover at the site of the seal are undesirable because the wrinkles can create areas in which cells can be trapped or which may result in leakage of cells.

Preferably, the device is rendered sterile prior to use. In one embodiment, each component of the present invention is sterilized prior to assembly of the device. Assembly of the present invention preferably is conducted under aseptic conditions. In another embodiment, a device of the present invention is sterilized following assembly. Suitable sterilization methods include, but are not limited to, gamma, ultra violet, or other radiation, dry heat, ethylene oxide, and steam, either alone or in combination. Steam sterilization is preferred.

Figure 3:
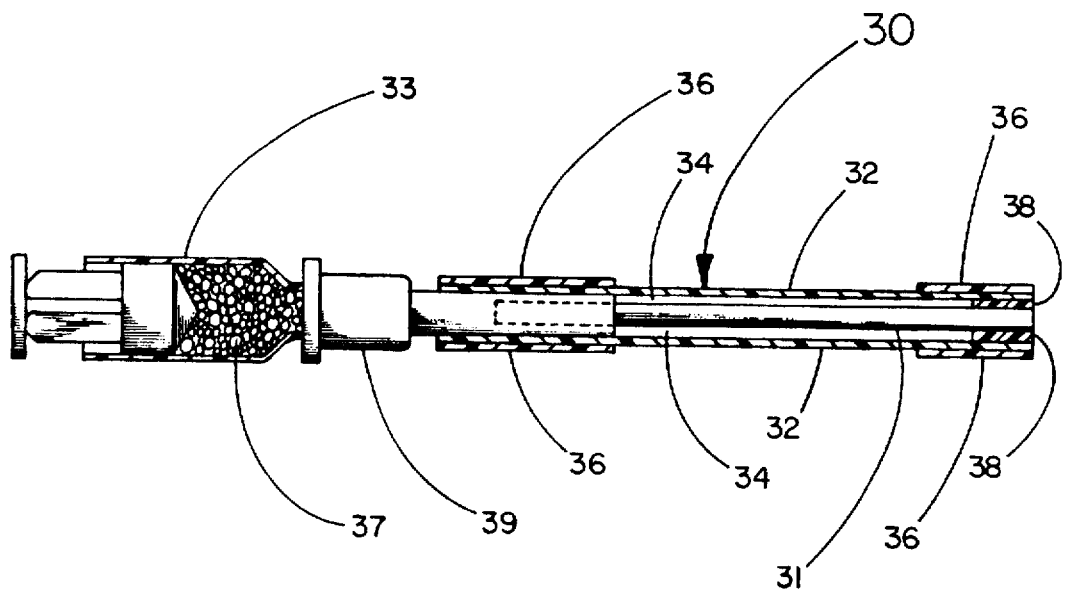
FIG. 3 illustrates the device assembly of FIG. 1 with a syringe 33 depicted in cross-section containing cells 37 to be loaded into device 30 through cell delivery device 39 attached to the assembly. Core 31, cover 32, sealing means 36, and spacer 38 are similar to components 11, 12, 16, and 18, respectively, of FIG. 1.
Figure 5:
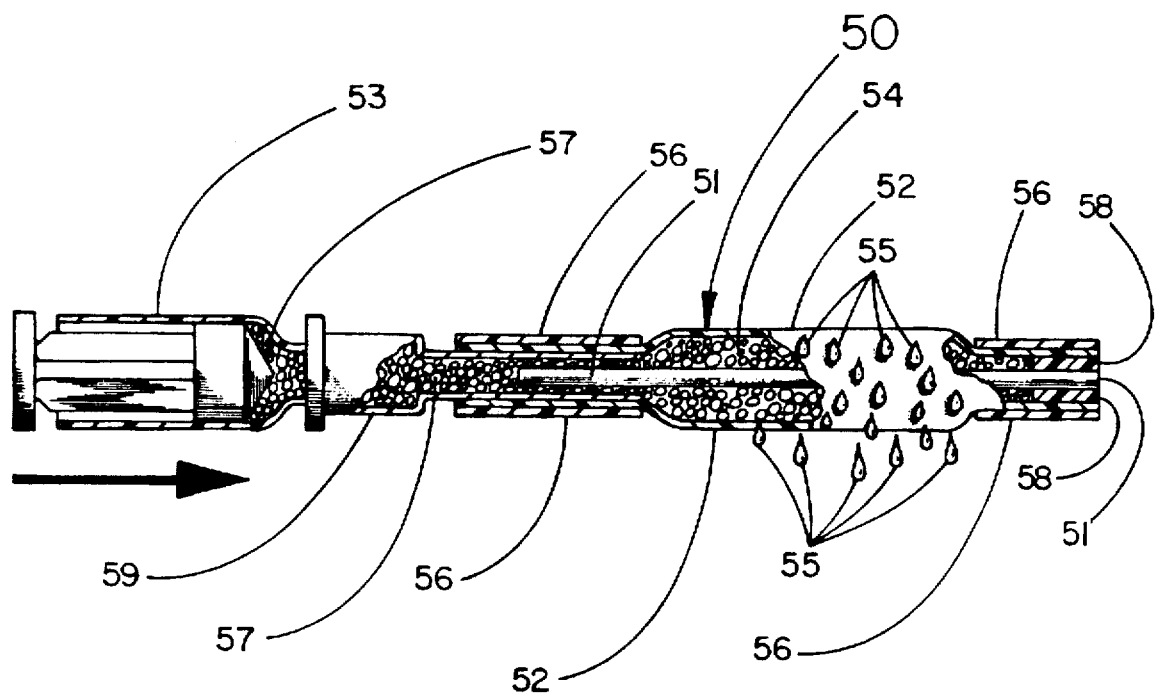
FIG. 5 illustrates a method of loading a device of the present invention 50 with cells 57 into the cell zone 54 between core 51 and cover 52 through cell delivery device 59 attached to a cell source 53 (e.g. a syringe). Sealing means 56 and spacer 58 are also depicted. In the Figure, some fluid 55 from the cell suspension is shown to have filtered through the cover 52, collected on the surface of the cover 52, and begun to weep from the cover 52.

In practice, a sterilized device of the present invention is attached to an aseptic syringe containing a cell suspension to be loaded into the device, as shown in FIG. 3. This procedure is performed under sterile conditions. As illustrated in FIG. 5, the syringe is then gently actuated to transfer the cell suspension into cell zone 54 of device 50 under a relatively low pressure (e.g., about 7 kPa to about 140 kPa) through the cell delivery device 59. As the cell suspension is introduced into cell zone 54, cells begin to fill cell zone 54 while the aqueous portion of the suspension contacts core 51 and cover 52. When contacted with the aqueous portion of the cell suspension, the core begins to rehydrate and expand from an initial first radial dimension to an enlarged second radial dimension. For most applications it is preferred that the dehydrated hydrogel core swells minimally in a longitudinal direction when hydrated. At substantially the same time, the cover spontaneously and substantially completely wets with liquid water. The normally opaque cover made of wetable agent-treated or surfactant-treated ePTFE becomes essentially translucent to transparent when wetted with liquid water. As a result, the loading of cells in the device can be observed and monitored visually through the cover.

Loading of cells into the device continues until the desired concentration of cells is achieved. In some applications, cells are sparsely loaded in the device and allowed to grow in the device. In other applications, cells are loaded in the device at high densities to substantially fill the device with cells. Due to the ability of cover 52 to weep, additional cell suspension can be introduced into cell zone 54 of the device without overflowing or bursting the device with the pressurized liquid component of the cell suspension. As a result, the cover is allowed to weep as much as needed while cells are loaded into the device to the desired concentration.

When device 50 is filled with the desired concentration of cells, the device is separated from the cell delivery device 59, as illustrated in FIG. 4. During this process, the open end of the device through which the cells were loaded is automatically sealed with sealing means 56. In order to separate device 50 from the cell delivery device 59, the cell delivery device is withdrawn from cover 52 and sealing means 56. As the cell delivery device 59 is withdrawn from sealing means 56, the sealing means, or constriction device, is actuated to constrict cover 52 against core 51 thereby sealing this open end of the device and encapsulating the cells contained therein.

When loading of the cells is finished and the cell delivery device 59 is withdrawn from device 50, sealing means 56, a portion of cover 52, and a portion of core 51 at the end of the device may be trimmed to ensure that any cells left in the open end of the device are removed. The trimmed end of the device may be cleaned or rendered sterile by various means, such as briefly swabbing the end with an ethanol solution, briefly touching the end with a heated instrument, or immersing the end into deionized, or distilled, water. The cell encapsulation device with its cache of cells can then be cultured in vitro or implanted in vivo.

Though the instant specification mentions the present invention is particularly suited for use to encapsulate cells for screening putative therapeutic substances and for gene therapy, there are numerous uses for the present invention wherein encapsulation of cells is desired. Suitable cells for use in the present invention include, but are not limited to, eukaryotic cells, such as cells that are autologous to a recipient, cells that are allogenic to a recipient, cells that are xenogenic to a recipient, gametes, and prokaryotic cells.

Without intending to limit the scope of the present invention, the following examples illustrate how the present invention can be made and used.

EXAMPLES

Example 1

A cover of the present invention was constructed in the form of a tube having a microporous polymeric film component comprised of multiple layers of oriented expanded polytetrafluoroethylene (ePTFE) film laminated together in multiple directions, relative to the principal axis of orientation of each ePTFE film layer.

An ePTFE film was used to make a laminated tube approximately 5 cm in length. The microporous film was made in accordance with U.S. Pat. Nos. 3,953,566 in the following manner and with the following properties. The film was first expanded in a single direction to form fibrils oriented primarily in the direction of expansion to produce an axially oriented film. This film was characterized by tensile strength of 10,000 psi, porosity of about 16 Gurley seconds, a width of about 6.0 mm, and a thickness of about 28.0 microns, as determined with a laser micrometer. The first of two film layers was applied to a 1.6 mm mandrel with the fibrils of the film oriented longitudinally with respect to the axis of the composite membrane. The second layer of film was wrapped on the first layer of film at approximately a 60° angle with respect to the first layer of film with a slight overlap of about 2 mm occurring between each successive helical wrap. The construction was heat bonded in an air convection oven set at 380° C. for approximately 5 minutes. The resultant cover was strong in all directions, retained its shape well, and was capable of filtering cells.

Example 2

This example illustrates the optional step of rendering the ePTFE material of Example 1 spontaneously and substantially completely water wettable by adsorbing and cross-linking the hydrophilic fluoropolymer poly(tetrafluoroethylene-co-vinyl alcohol) (HPL) into the microporous void spaces of the ePTFE material and onto the surfaces of the material.

The tubular ePTFE laminate described in Example 1 was immersed in 95% ethanol for about one minute to coat the surfaces and nearly completely fill the microporous void spaces of the material with the ethanol. The ePTFE material was removed from the ethanol solution and immediately placed in a solution of 1.5% (w/w) HPL in methanol:ethanol (4:1) for about 5 minutes. Care was taken not to let the ePTFE material become dry while transferring the material from one solution to another.

The ePTFE material was then removed from the HPL solution and blotted with a tissue or similar material to remove any excess solution. The HPL adsorbed ePTFE material was immersed in methanol for about 5 minutes, removed, blotted, and immersed again in methanol for about 5 minutes to wash any free HPL away. Care was taken not to let the ePTFE material become dry between transfers in the methanol solutions.

The methanol rinsed HPL adsorbed ePTFE material was further rinsed in deionized water for about 5 minutes. Again, the ePTFE material was not allowed to become dry between transfer of the material from the methanol solution to the deionized water.

The HPL copolymer impregnated in the microporous void spaces and covering the surfaces of the ePTFE material was fixed in situ by cross-linking the copolymer with glutaraldehyde. Upon removal of the ePTFE material from the deionized water rinse, the material was gently blotted and immediately placed in a prewarmed (i.e., about 80° C.) aqueous solution of 5% (v/v) glutaraldehyde (EM grade) with 1% (v/v) HCl as a catalyst. The cross-linking reaction was allowed to proceed for about 5 minutes at about 80° C. Following the cross-linking reaction, the ePTFE material was removed from the glutaraldehyde solution and immersed in deionized water for about 10 minutes to rinse any free glutaraldehyde away.

The hydrophilic fluoropolymer treated ePTFE material was then air dried and sterilized with steam.

Example 3

This example is similar to Example 2 except that polyvinyl alcohol was used as a hydrophilic polymeric wetting agent rather than HPL.

In the method, the ePTFE material of Example 1 was immersed in about 95% isopropanol for about 0.5 minutes to cover the surfaces and substantially completely fill the microporous void spaces of the ePTFE material with the isopropanol. Care was taken to ensure no air bubbles clung to the ePTFE material during this process.

The ePTFE material was removed from the isopropanol solution, gently blotted, and immersed in an aqueous solution of 1% polyvinyl alcohol (v/v) that was 100% hydrolyzed having a molecular weight of about 90 kg/mol. The ePTFE material was exposed to the polyvinyl alcohol solution for about 5 minutes. The ePTFE material was not allowed to dry out between transferal from the isopropanol solution to the polyvinyl alcohol solution. The ePTFE material was then removed from the polyvinyl alcohol solution, blotted, and immersed in deionized water for about 10 minutes to rinse any free polyvinyl alcohol away. The ePTFE material was not allowed to dry out between transferal from the polyvinyl alcohol solution to the deionized water.

The polyvinyl alcohol surfactant adsorbed in the microporous void spaces and covering the surfaces of the ePTFE material was fixed in situ by cross-linking the surfactant with glutaraldehyde. Upon removal of the ePTFE material from the deionized water rinse, the material was gently blotted, and immediately placed in an aqueous solution of 1–5% (v/v) glutaraldehyde (EM grade) and 1% (v/v) HCl for about 2 minutes.

Following the cross-linking reaction, the ePTFE material was removed from the glutaraldehyde solution and immersed in deionized water for about 10 minutes to rinse any free glutaraldehyde away.

The hydrophilic polymeric wetting agent treated ePTFE material was then air dried and sterilized with steam.

Example 4

A device of the present invention was assembled aseptically as follows. As described above, all components of the device are sterilized prior to assembly. Preferably, the components are steam sterilized. The hydrogel core, for example, was steam sterilized in a hydrated state and then dried under restraint in a sterile package.

Referring to FIG. 1, a dehydrated hydrogel core 12, having nominal dimensions of about 0.75 mm outer diameter (OD) when dehydrated and about 1.4 mm OD when hydrated, was inserted into a tubular cover 12 of Example 3 having a wall thickness of 50 µm, an average pore size of 0.3 µm, and porosity according to Gurley measurement of about 20 seconds, a nominal OD of about 1.62 mm with openings at both ends of the tube. A spacer 18 in the form of a ring made of poly(dimethyl siloxane) rubber with a nominal OD of about 1.19 mm and a nominal inner diameter (ID) of about 0.64 mm, was placed on one end of the core approximately 5 mm from the end. The core and the spacer were inserted into the cover with one end of the core protruding about 5 mm from the end of the cover. A sealing means 16 in the form of a constrictive silicone ring, approximately 10 mm in length, was placed around the cover as illustrated in FIG. 1 and allowed to constrict the cover against the sealing means.

A cell delivery device 19 in the form of a blunt-end stainless steel sixteen (16) gauge hypodermic needle, 3.81 cm long, was inserted into the opposite end of the tubular cover 12. The needle was placed within the cover in such a way that the core 11 inside the cover was inserted into the open blunt-end of the needle. The needle was inserted into the cover, over the core, so that the hypodermic needle penetrated about 5 mm into the lumen of the cover.

A sealing means 16, in the form of a constrictive silicone rubber ring, about 5 mm in length, was placed on the end of the cover having the hypodermic needle placed therein in such a way that the silicone constriction ring surrounded the end of the cover and the end of the hypodermic needle. When allowed to constrict, the silicone ring sealed the cover 12 against the cell delivery device 19.

Example 5

Cells were loaded into the device of Example 4 without spilling the cells or extrinsically contaminating the device as follows. Two cell suspensions were loaded into a device of the present invention in this example in order to demonstrate monitored and controlled loading of the cells into the device. Sterilized instruments, glassware, plasticware, cell culture media, and diluents were used while loading the device with cells.

A cell suspension was prepared in a volume of media that was approximately double the volume of the device, plus any unrecoverable volume associated with the cell delivery device. 300 μl of cell suspension was prepared in the present example. Once prepared, the cell suspension was placed in a 1 ml syringe. The syringe was purged of any air bubbles. A second 300 μl cell suspension in a 1 ml syringe was similarly prepared.

Large hemostatic forceps, or the like, were used to grasp and hold the hypodermic needle near the silicone rubber seal, but not on the cover of the device. After positioning the device in a generally horizontal orientation, the 1 ml syringe containing the cell suspension was connected to the hypodermic needle. The plunger on the syringe was slowly actuated to transfer the syringe contents into the cell zone of the device.

As the syringe contents entered the cell zone of the device, the dehydrated water swellable core began to rehydrate and swell in diameter. The cover of the device spontaneously became wet with liquid water and turned from an opaque appearance to a transparent appearance when contacted with the contents of the syringe. When the device became filled with the contents of the syringe, the culture media began to filter, or "weep" through the walls of the cover. Care was taken during this process not to over pressurize the device to the point of causing leakage of cell suspension through the seals.

Once the results of this first infusion of cells into the device were assessed and concluded to be acceptable, the first cell suspension containing syringe was removed from the hypodermic needle component of the device and the second cell suspension containing syringe was attached to the hypodermic needle in its place. Care was taken to avoid any air bubbles in the syringe tip or the hypodermic needle end from becoming entrained in the fluid path.

A second infusion of cells into the cell zone of the device was then performed as per the first infusion. The process was monitored through the transparent cover of the device until the device was filled with the desired amount of cells.

Once the cell zone was filled with cells, the syringe was disconnected from the Luer connector portion of the hypodermic needle and a Luer plug inserted in place of the syringe. The Luer-plugged end of the needle was immersed in deionized water to rinse and kill any cells that may have escaped at this junction. The cover of the device was not allowed to contact the deionized water.

The entire device was then immersed in sterile cell culture medium in a petri dish to a depth of about 4 mm and incubated at 37° C. for about one hour. During this time the hydrogel core continued to swell to its final outer diameter. Swelling of the core optimally positioned the encapsulated cells in the device for maximum viability and productivity.

In the end of the device having the spacer, the outer surface of the fully swollen core and the inner surface of the cover were in substantial, or near, contact in the region of the sealing means at this time. To complete the sealing process of this end of the device, the end of the device having the spacer was trimmed to remove the portion of the device containing the spacer and the accompanying cover and core portions. This resulted in sealing means 46 constricting cover 42 against core 41 as illustrated in FIG. 4.

The plugged hypodermic needle was removed from the cell encapsulation portion of the device by first grasping the hypodermic needle near the silicone seal, but not on the cover, with large hemostatic forceps. The Luer plug was then removed from the hypodermic needle to vent the assembly. Using rubber shod forceps, or the like, the device was grasped on the silicone seal near the hypodermic needle at a point very near to where the blunt end of the needle enters the seal. The device was positioned in a substantially horizonal orientation over a dry sterile field as the needle was slowly withdrawn from the cell encapsulation portion of the device with the large hemostatic forceps. As the needle was withdrawn from the cell encapsulation portion of the device, the silicone sealing ring automatically constricted and sealed the cover to the core of the device. During this part of the process, care was taken to confine any drops that emerged from the device to the end of the device near the seal and not allow any drops onto the cover of the device.

The newly sealed end of the cell encapsulation portion of the device was carefully trimmed with scissors to assure a tight seal and to prepare the end for sterilization to kill or remove any cells that may have escaped through the loading site. The trimmed end resulted in a silicone seal having a length of about 10 mm.

Once both ends of the device were trimmed, the sealed ends of the device were dipped in deionized water for about 20 seconds to kill any escaped cells. Care was taken to avoid placing the cover portion of the device into the deionized water.

To remove any cellular contaminants on the exterior of the device that may have been present after loading, the free standing cell encapsulation device was rinsed for several seconds in Hank's Balanced Salt Solution (HBSS).

The device was then placed in cell culture medium in a petri dish to a depth of about 4 mm and cultured at 37° C. for at least two hours prior to use.

Example 6

Cells encapsulated in devices of Example 5 were cultured in vitro as follows. Two devices were filled with rat insulinoma cells (RIN) cells. Two other devices were filled with CGT-6 cells. The two devices containing RIN cells were cultured in RPMI media containing 10% fetal bovine serum. The two devices containing the CGT-6 cells were cultured in OP-DMEM media. Each device was cultured in a T-25 tissue culture flask having a volume of about 4 ml of media. The cell containing devices were cultured for 17 days. Media was changed every day in each culture flask. At the end of the culture period, the devices were grossly examined for cell viability. Each device contained a viable cell population following in vitro culturing for over two weeks.

Example 7

Devices of Example 5 were implanted in each of three nude rats as follows. Each nude rat received two devices subcutaneously, one on each side of the peritoneal cavity. Each device was loaded with about $1 \times 10^5$ rat insulinoma cells (RIN) cells.

At two weeks, the devices were explanted from the rats and the cells encapsulated in the devices assayed for viability. Using a neutral red stain, cells in the device were determined to be viable.

While particular embodiments of the present invention have been illustrated and described herein, the present invention should not be limited to such illustrations and descriptions. It should be apparent that changes and modifications may be incorporated and embodied as part of the present invention within the scope of the claims.

What is claimed is:

1. A cell encapsulation device comprising:

A cell zone comprising a space delimited by a water wettable cover surrounding a cell displacing core within the cover;

wherein the cover has a coating thereon, the coating comprising a hydrophilic polymer material crosslinked to itself, wherein the cover is permeable to water and impermeable to cells such that the cover is a means to filter cells from solution upon introduction of cells and solution into the cell zone under a pressure less than about $6.9 \times 10^5$ Pa, thereby causing the solution to weep through the cover at a rate ranging from about 0.01 ml/cm$^2$/minute to about 100 ml/cm$^2$/minute while retaining the cells within the device;

wherein the core comprises a swellable material that expands form an initial first radial dimension to an enlarged second radial dimension upon exposure to an aqueous solution;

at least ne opening within the cover;

a cell delivery device to transfer cells into the device through the opening; and means to seal the opening following introduction of cells into the device.

2. The cell encapsulation device of claim 1 wherein the cell delivery device comprises a tube mounted in the opening adapted to transfer cells from a separate vessel into the device.

3. The cell encapsulation device of claim 1 wherein the means to seal the opening comprises a constrictive device at the opening that contracts to seal the opening automatically upon removal of the cell delivery device from the opening.

4. The cell encapsulation device of claim 1 wherein the swellable material has a first radial dimension that is at least 50% of the second radial dimension.

5. The cell encapsulation device of claim 1 wherein the cover turns essentially translucent to transparent upon introduction of an aqueous solution into the device.

6. The cell encapsulation device of claim 1 wherein the cover comprises at least one layer of a thin tape of expanded polytetrafluoroethylene.

7. The cell encapsulation device of claim 1 further comprising cells contained in the device.

8. A method for loading cells into a cell encapsulation device, the method comprising:

providing a cell encapsulation device comprising a cell zone comprising a space delimited by a water wettable cover surrounding a cell displacing core within the cover;

wherein the cover has a coating thereon, the coating comprising a hydrophilic polymer material crosslinked to itself, wherein the cover is permeable to water and impermeable to cells such that the cover is a means to filter cells from solution upon introduction of cells and solution into the cell zone under a pressure less than about $6.9 \times 10^5$ Pa, thereby causing the solution to weep through the cover at a rate ranging from about 0.01 ml/cm$^2$/minute to about 100 ml/cm$^2$/minute while retaining the cells within the device;

wherein the core comprises a swellable material that expands from an initial first radial dimension to an enlarged second radial dimension upon exposure to an aqueous solution;

at least one opening within the cover;

means to seal the opening following introduction of cells into the device;

providing a cell delivery device to transfer an aqueous solution of cells into the device form a separate vessel containing cells;

transferring the cells from the separate vessel into the cell encapsulation device under pressure; and allowing water to weep from the cover during the transferring of the cells, thereby concentrating the cells within the device.

9. The method of claim 8 that further comprises swelling the core following transfer of the cells into the device.

10. The method of claim 8 that further comprises providing a constrictive device at the opening to seal the opening of the device; and actuating the constrictive device to seal the opening following transfer of cells into the device.

* * * * *